US00PP12099P2

(12) United States Plant Patent
Westhoff

(10) Patent No.: US PP12,099 P2
(45) Date of Patent: Sep. 18, 2001

(54) SCAEVOLA PLANT NAMED 'BRILLANT'

(75) Inventor: Heinrich Westhoff, Südlohn (DE)

(73) Assignee: Gartenbau und Spezialkulturen Westhoff GbR, Südlohn-Oeding (DE)

( * ) Notice: Subject to any disclaimer, the term of this patent is extended or adjusted under 35 U.S.C. 154(b) by 0 days.

(21) Appl. No.: 09/592,378

(22) Filed: Jun. 12, 2000

(51) Int. Cl.[7] ..... A01H 5/00

(52) U.S. Cl. ..... Plt./363
(58) Field of Search ..... Plt./363

*Primary Examiner*—Bruce R. Campell
*Assistant Examiner*—June Hwu
(74) *Attorney, Agent, or Firm*—C. A. Whealy

(57) ABSTRACT

A distinctive cultivar of Scaevola plant named 'Brillant', characterized by its spreading, cascading and uniformly rounded plant habit; compact growth habit with short internodes; very freely branching plant habit; vigorous growth habit; and numerous blue purple fan-shaped flowers.

1 Drawing Sheet

BACKGROUND OF THE INVENTION

The present Invention relates to a new and distinct cultivar of Scaevola plant, botanically known as *Scaevola aemula* and referred to by the cultivar name Brillant.

The new cultivar is a product of a planned breeding program conducted by the Inventor in Sudlohn-Oeding, Germany. The new Scaevola originated from a cross of the Scaevola cultivar Fancy, disclosed in U.S. Plant Pat. No. 9,867, as the female, or seed, parent with an unidentified selection of *Scaevola aemula*, not patented, as the male, or pollen, parent. The new Scaevola was selected by the Inventor in 1998 on the basis of its compact plant habit.

Asexual reproduction of the new cultivar by terminal cuttings taken at Sudlohn-Oeding, Germany, has shown that the unique features of this new Scaevola are stable and reproduced true to type in successive generations.

SUMMARY OF THE INVENTION

The new cultivar has not been observed under all possible environmental conditions. The phenotype may vary somewhat with variations in environment such as temperature, daylength and light intensity, without, however, any variance in genotype.

The following characteristics have been repeatedly observed and are determined to be the basic characteristics of 'Brillant' which distinguish 'Brillant' as a new and distinct cultivar.

1. Spreading, cascading and uniformly rounded plant habit.

2. Compact plants with short internodes, dense and bushy plant form.

3. Very freely branching plant habit.

4. Vigrorous growth habit.

5. Very floriferous with numerous blue purple fan-shaped flowers.

Plants of the new Scaevola are most similar to the female parent, the cultivar Fancy. However in side-by-side comparisons conducted by the Inventor in Sudlohn-Oeding, Germany, plants of the new Scaevola and the cultivar Fancy differ in the following characteristics:

1. Plants of the new Scaevola are more compact and have shorter lateral branches than plants of the cultivar Fancy.

2. Plants of the new Scaevola are more freely branching than plants of the cultivar Fancy.

3. Plants of the new Scaevola have shorter internodes than plants of the cultivar Fancy.

4. Plants of the new Scaevola have more flowers per centimeter of lateral stem than plants of the cultivar Fancy.

5. Petal of the new Scaevola are not white at the base whereas petals of the cultivar Fancy are white at the base forming a white band.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which more accurately describe the actual colors of the new Scaevola. The photograph comprises a side perspective view of a typical hanging basket container of 'Brillant'.

DETAILED BOTANICAL DESCRIPTION

The following observations, measurements and values describe plants of the new Scaevola grown in containers in Sudlohn-Oeding, Germany under conditions which approximate those used in commercial production. Plants used for this description were about 8 weeks old and grown in 12.5-cm container during the spring in a glass-covered greenhouse. Color references are made to The Royal Horticultural Society Colour Chart except where general terms of ordinary dictionary significance are used.

Botanical classification: *Scaevola aemula* cultivar Brillant.
Parentage:

*Female, or seed, parent.*—*Scaevola aemula* cultivar Fancy, disclosed in U.S. Plant Pat. No. 9,867.

*Male, or pollen, parent.*—Unidentified selection of *Scaevola aemula*, not patented.

Propagation:

*Type cutting.*—Terminal cuttings.

*Time to develop roots.*—About four weeks at 22° C.

*Rooting habit.*—Fine, fibrous, and freely branching.

Plant description:

*Plant form and growth habit.*—Annual container and garden plant. Spreading, cascading and uniformly mounded plant habit; eventually plants become spherical in shape. Suitable for hanging basket, window box and patio containers. Compact plants with numerous leaves and short internodes; full, dense and bushy plant form. Very freely branching with lateral branches potentially forming at every vegetative leaf axil.

*Crop time.*—About 8 weeks are required to produce a finished, flowering plant in a 12.5-cm container.

*Vigor.*—Vigorous.

*Plant height* (*soil level to top of plant plane*).—About 22.5 cm.

*Plant length* (*soil level to apices of lateral branches*).—About 87.5 cm.

*Stem description.*—Lateral branch length: About 30 cm. Diameter: Main stems, about 5.5 mm; lateral branches, about 2.6 mm. Internode length: About 1.6 cm. Color: 144A, under high light, anthocyanin, 166A to 166B, is observed. Texture: Smooth; sparse pubescence.

*Foliage description.*—Arrangement: Alternate, single. Length: Fully expanded leaf, about 6.5 cm. Width: Fully expanded leaf, about 2 cm. Shape: Oblanceolate to spatulate. Apex: Acute. Base: Attenuate. Margin: Irregularly serrated, slightly serrated towards base and more strongly serrated towards apex. Texture: Very sparsely pubescent, rough and somewhat leathery, both surfaces. Color: Young leaves, upper surface: 137A to 137B. Young leaves, lower surface: 137C. Fully expanded leaves, upper surface: 137A to 137B. Fully expanded leaves, lower surface: 137C.

Flower description:

*Flower type and shape.*—Zygomorphic, semi-circular, fan-shaped flowers with five petals fused at the base to form a tubular flower throat. Flower throat open along the upper surface exposing reproductive organs. Flowers persistent. No fragrance detected.

*Flower arrangement and quantity.*—Solitary flowers arise from leaf axils with one flower per axil. Flowers held outwardly on upturned lateral apices. Flowering on about 24 cm of distal end of lateral stems. Very freely flowering, typically about 3 flowers per centimeter of flowering stem.

*Flowering time.*—Plants flower continuously from spring until frost. Flowers typically last at least 3 days on the plant.

*Flower buds.*—Shape: Lanceolate. Length: About 1.3 cm. Diameter: About 3 mm. Color: 145A becoming 148B to 148C just before opening.

*Perianth.*—Aspect: Fan-shaped, flat. Length, fan: About 3.75 cm. Width, fan: About 2 cm.

*Petals.*—Quantity: Five, fused at base. Shape: Close to oblanceolate. Apex: Cuspidate. Margin: Entire. Length, above tube: About 1.6 cm. Width, above tube: About 6 mm. Length, tube: About 1.4 cm. Diameter, tube opening: About 4 mm. Diameter, tube: About 2.5 mm. Texture: Smooth. Flower throat, whiskered. Color: When opening, upper surface: 90B. When opening, lower surface and tube: 90C. Fully opened, upper surface: 90C, veins, 79B. Fully opened, lower surface and tube: 90D, veins, 85D. Throat: 160A, veins, 200C. Tube: Upper surface, 199A, lower surface, 160D.

*Sepals.*—Quantity and arrangement: One large sepal, two smaller sepals lateral to larger sepal. Length: Larger sepal, about 1.75 cm; lateral sepals, about 9 mm. Width: Larger sepal, about 6 mm; lateral sepals, about 1.5 mm. Shape: Larger sepal, lanceolate; lateral sepals, acicular, needle-like. Apex: Acute. Margin: Enitre. Texture: Leathery, slightly pubescent, both surfaces. Color: Upper surface: 137A. Lower surface: 137C.

*Reproductive organs.*—Androecium: Five stamens. Anthers: Shape: Oval. Length: About 2 mm. Diameter: About 0.5 mm. Color: 166B. Pollen: Very scarce, yellow. Gynoecium: Pistil quantity: One. Pistil length: About 1.7 cm. Style length: About 1.2 cm. Style color: Apex, 166A; base, 145C. Stigma shape: Elongate. Stigma color: 155A. Ovary color: 145A.

*Seed.*—Seed production has not been observed.

Pest disease resistance: Plants of the new Scaevola have been noted to be resistant to pest/pathogens common to Scaevola.

Weather tolerance: Plants of the new Scaevola have been observed to be tolerant to rain and wind.

It is claimed:

1. A new and distinct Scaevola plant named 'Brillant', as illustrated and described.

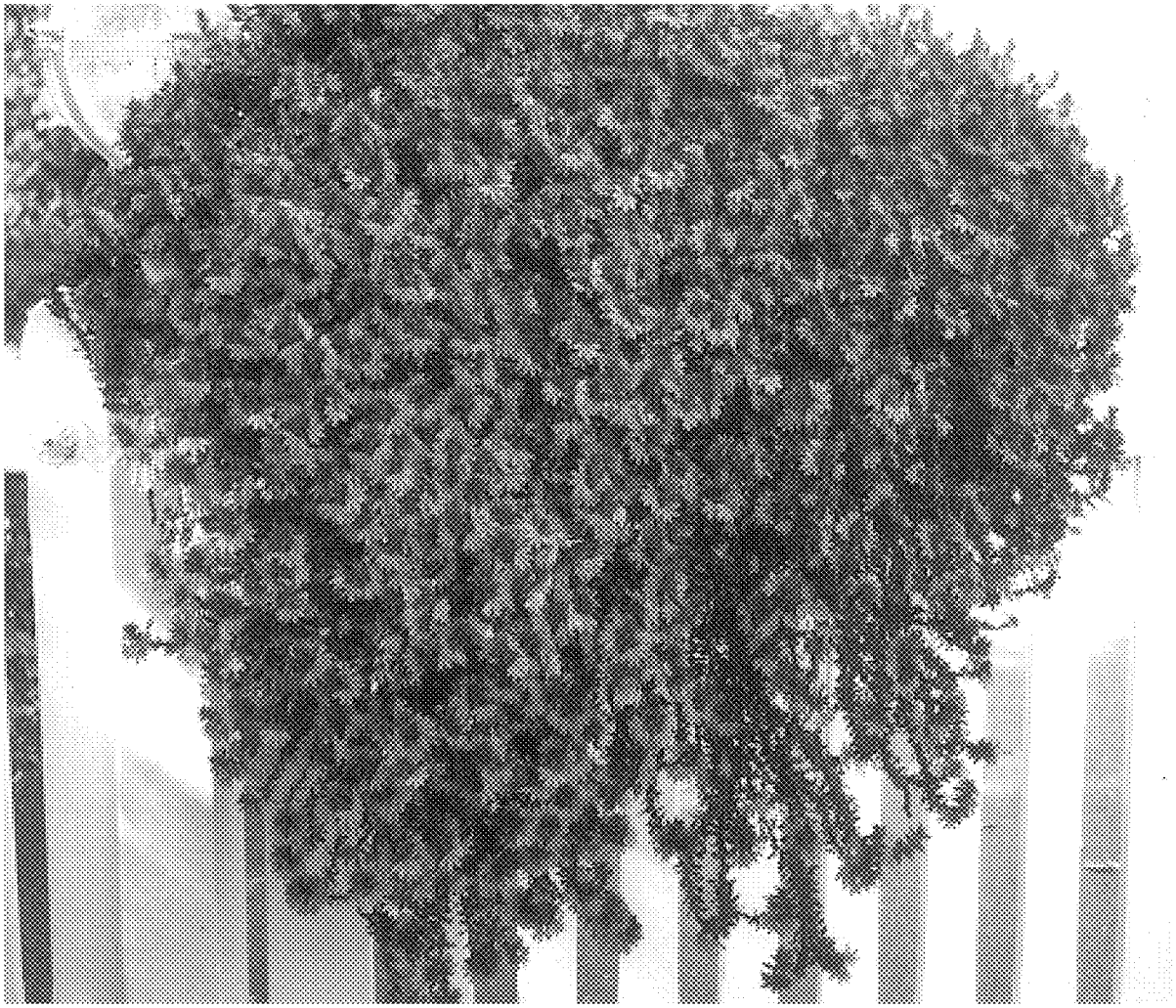

* * * * *